United States Patent [19]

Gustavsson et al.

[11] Patent Number: 4,797,472

[45] Date of Patent: Jan. 10, 1989

[54] NEW PEPTIDE DERIVATIVES

[75] Inventors: Stig I. Gustavsson, Mölndal; Salo Arielly, Kungsbacka, both of Sweden

[73] Assignee: KabiVitrum AB, Stockholm, Sweden

[21] Appl. No.: 27,969

[22] Filed: Mar. 19, 1987

[30] Foreign Application Priority Data

Mar. 21, 1986 [SE] Sweden ............................ 8601329

[51] Int. Cl.⁴ ................................................ C07K 5/08
[52] U.S. Cl. ...................................... 530/331; 530/802
[58] Field of Search ................................ 530/331, 802

[56] References Cited

U.S. PATENT DOCUMENTS

| | | | |
|---|---|---|---|
| 4,275,153 | 6/1981 | Garginlo et al. | 530/331 |
| 4,336,186 | 6/1982 | Garginlo et al. | 530/331 |
| 4,440,678 | 4/1984 | Svendsen | 530/331 |
| 4,508,644 | 4/1985 | Heber et al. | 530/331 |
| 4,622,389 | 11/1986 | Nagasawa et al. | 530/331 |
| 4,665,016 | 5/1987 | Heber et al. | 435/23 |

FOREIGN PATENT DOCUMENTS 3428543 2/1986 Fed. Rep. of Germany .
8601209 2/1986 PCT Int'l Appl. .

Primary Examiner—Delbert R. Phillips
Assistant Examiner—Christina Chan
Attorney, Agent, or Firm—Pollock, Vande Sande & Priddy

[57] ABSTRACT

Tripeptide derivatives, characterized by the general formula:

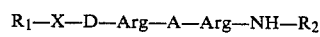

wherein $R_1$ is hydrogen, α- or β-naphtyl residue, lower alkyl residue which may be substituted with a carboxyl group, unsubstituted or substituted phenyl- or phenylalkyl residue.

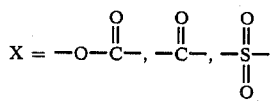

or a single bond with the proviso that when $R_1$ is hydrogen then and only then X is a single bond
A=Gly or Sar
$R_2$=an aromatic or heterocyclic residue which gives a compound $R_2$—$NH_2$ by enzymatic hydrolysis, which can be determined quantitatively
or disalts and trisalts of inorganic or organic acids thereof, process for their preparation and method for determination of serine proteases, especially Factor $X_a$,
or components which can interact with serine proteases or zymogen forms thereof.

22 Claims, No Drawings

NEW PEPTIDE DERIVATIVES

TECHNICAL FIELD

The present invention relates to novel tripeptide derivatives useful for determination of serine proteases. The novel derivatives are especially suitable for determination of Factor $X_a$ (E.C.3.4.21.6) or for analyses of reactions, in which $FX_a$ is formed, inhibited or consumed which makes it possible to quantify other enzymes and/or inhibitors present in the reactions.

THE BACKGROUND OF THE INVENTION

Factor $X_a$ is a key substance in the reaction cascade which leads to the blood coagulation. Several methods based on the determination of $FX_a$ with chromogenic substrate have shown to be of considerable value within the clinical diagnostic in explanation of disturbances in the blood coagulation system (Hemker H. C.—Handbook of synthetic substrates, 1983, Martinus Nijhoff Publishers, Boston).

PRIOR ART

Chromogenic tetrapeptide derivatives are described by Aurell, L., et al. (Haemostasis vol. 7, 1978, 92-94) and have shown to be of considerable value in this case. These substrates are based on the amino acid sequence (—Ile—Glue—Gly—Arg—), which precedes the splitting places in the natural substrate prothrombin. The tetrapeptide substrates are characterized by high selectivity i.e. other enzymes, especially thrombin, do not disturb the determination of Factor $X_a$. Disadvantages are however the limited solubility and the several steps in the synthesis. EP No. 34 122 shows that tripeptide derivatives may be useful as $FX_a$ substrates. However, these tripeptides are sensitive to thrombin too. The high selectivity of the tetrapeptides is not obtained by these tripeptides.

DESCRIPTION OF THE INVENTION

The tripeptide derivatives in the present invention show high sensitivity and solubility and simultaneously selectivity properties comparable with the tetrapeptides in the prior art. The novel substrates are characterized by the following formula:

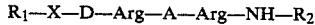

R$_1$—X—D—Arg—A—Arg—NH—R$_2$ wherein $R_1$ is hydrogen, α- or β-naphthyl residue, lower alkyl residue which may be substituted with a carboxyl group, unsubstituted or substituted phenyl- or phenylalkyl residue, wherein the alkyl group having 1 to 4 carbon atoms and preferably wherein the substitution is in para position in the phenyl ring and the substituents are lower alkyl, lower alkoxy, halogen or nitro group;
  lower alkyl is a straight or branched alkyl group having 1 to 4 carbon atoms, preferably methyl, ethyl or tert. butyl;
  lower alkoxy is an alkoxy group having 1 to 4 carbon atoms, preferably methoxy;
  halogen is chlorine, bromine, fluorine, or iodine, preferably chlorine;

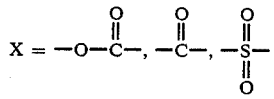

or a single bond with the proviso that when $R_1$ is a hydrogen then and only then X is a single bond
A = Gly or Sar
$R_2$ = an aromatic or heterocyclic residue which gives the compound $R_2$—NH$_2$ by enzymatic hydrolysis or di- and tri-salts of inorganic or organic acids thereof.

These compounds $R_2$—NH$_2$ are prior known compounds with chromogenic, fluorogenic or electrochemical properties which permit quantifying of serine proteases by determination of splitted marker directly or after derivatization (Hemker H. C., loc. cit. and references cited therein).

Examples of compounds $R_2$—NH$_2$ are: p-nitroaniline, 3-carboxy-4-hydroxyaniline, 3-sulfo-4-nitroaniline, 3-alkoxy-4-nitroaniline, 3-carboxy-4-nitroaniline, 4-methoxy-β-naphtylamine, 4-(N-ethyl-N-hydroxyethyl)aminoaniline, 5-amino-isophtalic acid-dimethyl ester, 5-amino-8-nitroquinoline, 7-amino-4-trifluoromethyl coumarine, 7-amino-4-methyl coumarine, 4-aminodiphenylamine.

The novel derivatives containing two amino acids with strong basic side-chain can form disalts or when $R_1$ is hydrogen trisalts with inorganic or organic acids. Preferred salts are disalts of inorganic or organic acids since they possess a high water solubility. Especially preferred salts are hydrochlorides.

The splitting of the substrates by the appropriate enzymes for determination takes place on the carboxylic side of arginine in L-form, therefore the N-terminal arginine must be as D-isomer. Surprisingly, at biological pH the negatively charged or neutral lipophilic part of the tetrapeptide substrate could be changed to a positively charged strong basic amino acid with retained high selectivity and increased sensitivity.

The use of the peptide derivatives according to the present invention in methods for quantitative and/or qualitative determination of serine proteases or quantitative and/or qualitative determination of components, which can interact with serine proteases or zymogen forms thereof, such as Factor X which is activated to Factor $Z_a$, are important applications.

The novel Factor $X_a$ substrates constitute by their sensitivity, high solubility and good selectivity a valuable addition at the establishment of diagnostic analyses based on determination of Factor $X_a$. A good selectivity is an important criterion in determination of $FX_a$ in plasma, since there is otherwise a risk of influence from thrombin which may be present initially or formed during the assay. Examples of important applications are determination of $FX_a$ in human plasma, after activation with a protease from Russel's Viper Venom (RVV-X), of antifactor $X_a$, of heparin, and of FVIII:C at hemophilia (Hemker H. C., loc. cit., S. Rosén, Scand. J. Haematol. Suppl. 40, vol. 33, 1984, 139–145). Especially important applications are analyses in connection with anticoagulantia treatment with low molecular weight heparin fractions, where traditional clot-based methods cannot be used. (Walenga J. M. et al., Seminars in Thrombosis and Hemostatis, vol. 11, no. 2, 1985, 100–107). Specifically included are methods relying upon determination of $FX_a$-activity and used for the direct determination of FX and $FX_a$ or for the indirect determination of FVII, $FVII_a$, FVIII:C, $FVIII:C_a$, FIX, $FIX_a$, antithrombin III, platelet factor 4, heparin, low molecular weight heparins and heparinoids. The properties of the novel substrates make them especially suitable for use in automatic analyzers.

DESCRIPTION OF SYNTHESIS

At the synthesis of the novel $FX_a$ substrates conventional protecting groups and coupling methods within the peptide chemistry are used (M. Bodansky: "Principles of Peptide Synthesis", Springer Verlag 1984), e.g. addition step-by-step of the amino acids at the C-terminal amino acid provided with a marker, or synthesis of the N-terminal peptide fragment per se, which then is coupled to the C-terminal amino acid provided with a marker.

Useful amino protecting groups are benzyloxycarbonyl-, 9-fluorenylmethyloxycarbonyl- or t-butyloxy-carbonyl groups. To protect the guanidino group of the arginine is used protonisation, a nitro-protecting group or a p-toluenesulfonyl protecting group. The coupling between the amino acids is performed by activation of the α-carboxylic group (e.g. active esters, symmetric or asymmetric anhydrides, azide, DCCI or related reagents).

The invention will be described more in detail in the following not limited working examples, which show the preparation of different substrates according to the invention.

Purification of the intermediates and end products is performed by precipitation, crystallization or gel filtration chromatography. The purified end products are lyophilized. Prefabricated glass plates of silica gel $F_{254}$ are used in the TLC analyses. After terminated chromatography the plates are inspected in UV light (254 nm) and are then developed with ninhydrin and chlorine/dicarboxidine reagent. The $R_f$-values given are results from single chromatographies.

Solvent systems used for TLC are indicated according to the following table

| Indication | Solvent system | Volume ratio |
|---|---|---|
| A = | n-butanol: AcOH: water | (3:2:1) |
| Pa6 = | chloroform: MeOH: AcOH: water | (34:4:9:2) |
| M = | n-butanol: AcOH: water: pyridine | (15:3:12:10) |
| "3" = | EtOAc: AcOH: water: pyridine | (30:6:11:20) |

HPLC analyses were performed on Merck RP column (Hibar LiChraCart) with 40% MeOH in 0.5% triethylaminophosphate pH=2.35 as eluant (1 ml/min). The optical activity of the end products are determined at 589 nm in 50% acetic acid at a concentration of 0.4–1.0 g/100 ml and +25° C.

The below mentioned abbreviations have the following meaning: (IUPAC indication has been used where such exists).

Amino acids:
Arg=arginine
D-Arg=D-arginine
Gly=glycine
Sar=sarcosine (N-methylglycine)

All amino acids in the substrates have L-configuration if nothing else is indicated.

The free amino acid or peptide is indicated by H- at the N-terminal amino group and -OH at the carboxyl terminal group. The amino group is always given to the left and the carboxyl group to the right.

ABBREVIATIONS

Ac=acetyl
AcOH=acetic acid
AMC=7-amino-4-methylcoumarine
Box=t-butyloxycarbonyl
Bs=benzenesulfonyl
Bz=benzoyl
Bzls=benzylsulfonyl
CHA=3-carboxy-4-hydroxyanilide
4-ClBs=4-chlorobenzenesulfonyl
DCCI=dicyclohexylcarbodiimide
DCU=dicyclohexylurea
DMF=dimethylformamide
Eoc=ethyloxycarbonyl
EtOAc=ethylacetate
EtOH=ethanol
$Et_3N$=triethylamine
Ets=ethanesulfonyl
HOBT=1-hydroxybenzotriazole
HPLC=High Performance Liquid Chromatography
I=ionic strength
Mbs=4-methoxybenzenesulfonyl
MeOH=methanol
Mes=methanesulfonyl
Moz=4-methoxybenzyloxycarbonyl
4-Nbs=4-nitrobenzenesulfonyl
NEM=4-ethylmorpholine
4-Nz=4-nitrobenzyloxycarbonyl
Ps=β-naphtalenesulfonyl
ONp=p-nitrophenylester
pNA=p-nitroaniline
Suc=succinyl
TFA=trifluoroacetic acid
TLC=Thin Layer Chromatography
Tos=p-toluenesulfonyl
Tris=tris(hydroxymethyl)aminomethane
Z=benzyloxycarbonyl

WORKING EXAMPLES

EXAMPLE 1

$N^\alpha$—Z—D—Arg—Gly—Arg—pNA.2HCl 

Molecular weight=714.62

(1a) Boc-Gly—Arg—pNA.HBr

Molecular weight=532.40

43 mmol H—Arg—pNA.2HBr dissolved in 120 ml DMF is neutralized in cold (−10° C.) with $Et_3N$. The $Et_3N$.HBr formed is filtered off, whereafter 43 mmol Box—Gly—OH, 45 mmol HOBT and 50 mmol DCCI are added. The reaction goes on during stirring for 1 hour in cold and at room temperature overnight. The DCU formed is filtered off and the solution is evaporated in vacuo to an oil which is dissolved in 160 ml EtOAc, is washed with 2% $NaHCO_3$, $H_2O$, 2% $KHSO_4$ and $H_2O$. After drying with $Na_2SO_4$ the EtOAc-phase is evaporated and precipitated with diethylether.

Yield: 71%

TLC: Rf=0.23 ($Pa_6$).

(1b) H—Gly—Arg—pNA.TFA.HBr

Molecular weight=546.36

55 ml TFA is added to 30 mmol Boc—Gly—Arg—p-NA.HBr (prepared according to Example 1a) dissolved in 55 ml methylenechloride. The mixture is stirred for 30 minutes at room temperature and is precipitated with diethylether thereafter.

Yield: ~100%
TLC: Rf=0.28 (A).

1. $N^\alpha$—Z—D—Arg—Gly—Arg—pNA.2HCl

Molecular weight=714.62

2.5 mmol Z—D—Arg—OH.HCl, 3 mmol HOBT and 3 mmol DCCI are added to 2.5 mmol H—Gly—Arg—pNA—TFA.HBr (prepared according to Example 1b) dissolved in 25 ml DMF and neutralized in cold (−10° C.) with Et$_3$N. The mixture is stirred for 1 hour in cold and for 48 hours at room temperature. The DCU formed is filtered off and the solution is evaporated in vacuo to an oil, 30 ml water is added and the solution is washed with 2×20 ml EtOAc. The water phase is evaporated in vacuo, the product is ion exchanged on a Sephadex® QAE-25 column, in chloride form with 50% EtOH as eluent and is purified on a Merck Lobar® prepacked column (LiChroprep®.RP-8-B) with 30% MeOH as eluent (2 ml/min.) at the end. The purified product is lyophilized.

Yield: 37%
TCL: Rf=0.11 (Pa$_6$)
HPLC: 98.5% purity
$[\alpha]=-18.1°$ (c=0.5%).

EXAMPLE 2

$N^\alpha$—Boc—D—Arg—Gly—Arg—pNA.2HCl

Molecular weight=680.59

2.5 mmol H—Gly—ARg—pNA.TFA.Hbr and 2.5 mmol Boc—D—Arg—OH HCl are treated with the same coupling method and reaction conditions as in example 1.

Yield: 35%
TLC: Rf=0.55 (M)
HPLC: 96% purity
$[\alpha]=-25.5°$ (c=0.4%).

EXAMPLE 3

H—D—Arg—Gly—Arg—pNA.3HCl

Molecular weight=616.96

22 ml TFA is added to 12 mmol $N^\alpha$—Boc—D—Arg—Gly—Arg—pNA.2HCl (prepared according to example 2) dissolved in 22 ml methylenechloride. The mixture is stirred for 30 minutes at room temperature and precipitated with diethylether thereafter. The product is ion exchanged and purified in the same way as in example 1.

Yield: 38%
TLC: Rf=0.30 (M)
HPLC: 98% purity
$[\alpha]=-62.4°$ (c=0.5%).

EXAMPLE 4

$N^\alpha$—Ets—D—Arg—Gly—Arg—pNA.2HCl

Molecular weight=672.62

0.5 mmol ethanesulfonylchloride and 80 μl Et$_3$N are added to 0.5 mmol H—D—Arg—Gly—Arg—pNA.3HCl (prepared according to example 3) dissolved in 10 ml DMF and neutralized in cold (−10°) with 80 μl Et$_3$N. The reaction goes on during stirring for 1 hour in cold and for 2 hours at room temperature. The mixture is evaporated in vacuo. The product is ion exchanged and purified in the same way as in example 1.

Yield: 44%
TLC: RF=0.5 (M)
HPLC: 9% purity
$[\alpha]=-15.6°$ (c=0.65%).

EXAMPLE 5

$N^\alpha$—Bs—D—Arg—Gly—Arg—pNA.2HCl

Molecular weight=720.66

0.5 mmol H—D—Arg—Gly—Arg—pNA.3HCl (prepared according to example 3) and 0.5 mmol benzenesulfonylchloride are treated in the same way and under the same reaction conditions as in example 4.

Yield: 37%
TLC: Rf=0.53 (M)
HPLC: 98% purity
$[\alpha]=+11.6°$ (c=0.45%).

EXAMPLE 6

$N^\alpha$—4—Nz—D—Arg—Gly—Arg—pNA.2HCl

Molecular weight=759.64

0.5 mmol H—D—Arg—Gly—Arg—pNA.3HCl (prepared according to example 3) and 0.5 mmol 4-nitrobenzyloxycarbonylchloride are treated in the same way and under the same reaction conditions as in example 4.

Yield: 57%
TLC: Rf=0.3 (A)
HPLC: 99% purity
$[\alpha]=-20.2°$ C. (c=0.45%).

EXAMPLE 7

$N^\alpha$—4—Nbs—D—Arg—Gly—Arg—pNA.2HCl

Molecular weight=765.66

0.5 mmol H—D—Arg—Gly—Arg—pNA.3HCl (prepared according to example 3) and 0.5 mmol 4-nitrobenzensulfonylchloride are treated in the same way and under the same reaction conditions as in example 4.

Yield: 25%
TLC: Rf=0.28 (A)
HPLC: 97% purity
$[\alpha]=-0.8°$ (c=0.6%).

EXAMPLE 8

$N^\alpha$—Tos—D—Arg—Gly—Arg—pNA.2HCl

Molecular weight=734.69

0.5 mmol H—D—Arg—Gly—Arg—pNA.3HCl (prepared according to example 3) and 0.5 mmol p-toluenesulfonylchloride are treated in the same way and under the same reaction conditions as in example 4.

Yield: 45%
TLC: Rf=0.25 (A)
HPLC: 98% purity
$[\alpha]=+23.1°$ (c=0.45%).

EXAMPLE 9

$N^\alpha$—Moz—D—Arg—Gly—Arg—pNA.2HCl

Molecular weight=744.66

0.5 mmol H—D—Arg—Gly—Arg—pNA.3HCl (prepared according to example 3) and 0.5 mmol 4-methyloxybenzyloxycarbonylazide are treated in the same way and under the same reaction conditions as in example 4.

Yield: 31%
TLC: Rf=0.22 (A)
HPLC: 97% purity
$[\alpha]=-15.9°$ (c=0.4%).

EXAMPLE 10

N$^\alpha$—Mbs—D—Arg—Gly—Arg—pNA.2HCl

Molecular weight=750.69

0.5 mmol H—D—Arg—Gly—Arg—pNA.3HCl (prepared according to example 3) and 0.5 mmol 4-methoxybenzenesulfonylchloride are treated in the same way and under the same reaction conditions as in example 4.

Yield: 45%
TLC: Rf=0.31 (A)
HPLC: 99% purity
[α]=+22.8° (C=0.4%).

EXAMPLE 11

N$^\alpha$—4—ClBs—D—Arg—Gly—Arg—pNA.2HCl

Molecular weight=755.12

0.5 mmol H—D—Arg—Gly—Arg—pNA.3HCl (prepared according to example 3) and 0.5 mmol 4-chlorobenzenesulfonylchloride are treated in the same way and under the same reaction conditions as in example 4.

Yield: 31%
TLC: Rf=0.38 (A)
HPLC: 99% purity
[α]=+10.9° (c=0.4%).

EXAMPLE 12

N$^\alpha$—Ns—D—Arg—Gly—Arg—pNA.2HCl

Molecular weight=770.73

0.5 mmol H—D—Arg—Gly—Arg—pNA.3HCl (prepared according to example 3) and 0.5 mmol β-naphthalenesulfonylchloride are treated in the same way and under the same reaction conditions as in example 4.

Yield: 25%
TLC: Rf=0.29 (A)
HPLC: 99% purity
[α]=−21.5° (c=0.4%).

EXAMPLE 13

N$^\alpha$—Z—D—Arg—Gly—Arg—AMC—.2HCl

Molecular weight=751.70

2 mmol Z—D—Arg—Gly—OH.HCl, 2.5 mmol HOBT and 2.5 mmol DCCI are added to 2 mmol H—Arg—AMC.2HCl dissolved in 30 ml DMF and neutralized in cold (−10° C.) with Et$_3$N. The reaction is performed during stirring for 1 hour in cold and for 24 hours at room temperature. The DCU formed is filtered off and the solution is evaporated in vacuo to an oil, which is ion exchanged and purified in the same way as in example 1.

Yield: 39%
TLC: Rf=0.7 ("3")
HPLC: 99% purity
[α]=−28.6° (c=0.5%).

EXAMPLE 14

N$^\alpha$—Ac—D—Arg—Gly—Arg—pNA.2HCl

Molecular weight=622.54

0.5 mmol H—D—Arg—Gly—Arg—pNA.3HCl (prepared according to example 3) and 0.5 mmol acetic acid anhydride are treated in the same way and under the same reaction conditions as in example 4.

Yield: 43%
TLC: Rf=0.45 (M)
HPLC: 97% purity
[α]=−27.9° (c=0.4%).

EXAMPLE 15

N$^\alpha$—Suc—D—Arg—Gly—Arg—pNA.2HCl

Molecular weight=680.57

0.5 mmol H—D—Arg—Gly—Arg—pNA.3HCl (prepared according to example 3) and 0.5 mmol succinic acid anhydride are treated in the same way and under the same reaction conditions as in example 4.

Yield: 40%
TLC: Rf=0.23 (A)
HPLC: 98% purity
[α]=−21.4° (c=0.5%).

EXAMPLE 16

N$^\alpha$—Bzls—D—Arg—Gly—Arg—pNA.2HCl

Molecular weight 734.69

0.5 mmol H—D—Arg—Gly—Arg—pNA.3HCl (prepared according to example 3) and 0.5 mmol benzylsulfonylchloride are treated in the same way and under the same reaction conditions as in example 4.

Yield: 38%
TLC: Rf=0.26 (A)
HPLC: 98% purity
[α]=−7.8 (c=0.4%).

EXAMPLE 17

N$^\alpha$—Bz—D—Arg—Gly—Arg—pNA.2HCl

Molecular weight=684.61

(17a) Z—Gly—Arg(NO$_2$)—pNA

Molecular weight=530.51

0.35 mol H—Arg—(NO$_2$)pNA.HBr dissolved in 750 ml DMF is neutralized in cold (−10° C.) with Et$_3$N. The Et$_3$N.HBr formed is filtered off, whereafter 0.35 mol Z—Gly—OH, 0.35 mol HOBT and 0.38 mol DCCI are added. The reaction is performed during stirring for 1 hour in cold and at room temperature overnight. The DCU formed is filtered off and the solution is evaporated in vacuo to an oil, which is triturated with 3×400 ml 2% NaHCO$_3$ and 500 ml water. The product is recrystallized from 3.5 l MeOH.

Yield: 80%
TLC: Rf=0.6 (Pa$_6$).

(17a) H—Gly—Arg(NO$_2$)—pNA.HCl

Molecular weight=432.72

0.3 mol Z—Gly—Arg(NO$_2$)—pNA (prepared according to example 17a) is suspended in 630 ml AcOH. 415 ml 5.6M HBr in AcOH is added during stirring. The mixture is stirred for 45 minutes at room temperature and poured into 7.5 l dry diethylether during stirring. The precipitate is filtered, washed with diethylether and dried in vacuo.

Yield: 90%

3 g product is ion exchanged in the same way as in example 1.

Yield: 73%
TLC: Rf=0.15 (Pa$_6$).

(17a) N$^\alpha$—Boc—D—Arg(NO$_2$)—Gly—Arg(NO$_2$)—pNA

Molecular weight=697.69

4 mmol H—Gly—Arg(NO$_2$)—pNA.HCl (prepared according to example 17b) dissolved in 25 ml DMF is neutralized in cold (−10° C.) with Et$_3$N. The Et$_3$N.HCl formed is filtered off, whereafter 4 mmol α—Box—D—Arg(NO$_2$)—OH, 4mmol HOBT and 4.2 mmol DCCI are added. The reaction is performed during stirring for 1 hour in cold and at room temperature over the night. The DCU formed is filtered off and the solution is evaporated in vacuo to an oil, which is suspended with 2% NaHCO$_3$, water, 2% KHSO$_4$, water and diethylether.

Yield: 73%
TLC: Rf=0.32 (Pa$_6$).

(17d) H—D—Arg(NO$_2$)—Gly—Arg(NO$_2$)—p-NA.HCl

Molecular weight=634.04

3 mmol N$^\alpha$—Box—D—Arg—(NO$_2$)—Gly—Arg(NO$_2$)—pNA (prepared according to example 17c) is suspended in 11 ml AcOH, 11 ml TFA is added and the mixture is stirred for 4 hours at room temperature. The product is precipitated with diethylether and ion exchanged in the same way as in example 1.

Yield: 72%
TLC: Rf=0.61 (M)

(17e) N$^\alpha$—Bz—D—Arg(NO$_2$)—Gly—Arg(NO$_2$)—pNA

Molecular weight=701.68

0.6 mmol benzoic anhydride and 70 μl Et$_3$N are added to 0.5 mmol H—D—Arg(NO$_2$)—Gly—Arg(NO$_2$)—pNA.HCl (prepared according to example 17d) dissolved in 20 ml DMF and neutralized in cold (−10° C.) with 70 μl Et$_3$N. The reaction is performed during stirring for 1 hour in cold and for 2 hours at room temperature. The mixture is evaporated in vacuo and precipitated with water. The product is suspended with 30 ml warm MeOH, is filtered and dried.

Yield: 68%
TLC: Rf=0.31 (Pa$_6$).

17. N$^\alpha$—Bz—D—Arg—Gly—Arg—pNA2HCl
Molecular weight=684.61

0.35 mmol N$^\alpha$—Bz—D—Arg(NO$_2$)—Gly—Arg(NO$_2$)—pNA (prepared according example 17e) is deprotected by reaction with 15 ml dry HF in presence of 0.5 ml anisole. in a suitable apparatus according to Sakakibara (S. Sakakibara et al. Bull. Chem. Soc., Japan vol. 240 p. 7164–67, 1967) for 60 minutes at 0° C. After terminated reaction all HF is distilled and the raw product is ion exchanged and purified in the same way as in example 1.

Yield: 36%
TLC: Rf=0.55 (M)
HPLC: 98% purity
[α]=−24.4° (c=0.6%).

EXAMPLE 18

N$^\alpha$—Eoc—D—Arg—Gly—Arg—pNA.2HCl

Molecular weight=652.57

(18a) N$^\alpha$—Eoc—D—Arg(NO$_2$)—Gly—Arg(NO$_2$)—pNA

Molecular weight=669.63 0.6 mmol ethylchloroformate and 70 μl Et$_3$N are added to 0.5 mmol H—D—Arg(NO$_2$)—Gly—Arg(NO$_2$)—pNA.HCl (prepared according to example 17d) dissolved in 20 ml DMF and neutralized in cold (31 10° C.) with 70 μl Et$_3$N. The reaction goes on during stirring for 1 hour in cold and for 2 hours at room temperature. The mixture is evaporated in vacuo and precipitated with water, filtrated and washed with water and diethylether.

Yield: 89%
TLC: Rf=0.26 (Pa$_6$).

(18) N$^\alpha$—Eoc—D—Arg—Gly—Arg—pNA.2HCl
Molecular weight=652.57

0.45 mmol N$^\alpha$—Eoc—D—Arg(NO$_2$)—Gly—Arg(NO$_2$)—pNA (prepared according to example 18a) is deprotected by reaction with 20 ml dry HF in presence of 0.5 ml anisole in the same way as in example 17.

Yield: 41%
TLC: Rf=0.55 (M)
HPLC: 98% purity
[α]=−25.2° (c=0.35%).

EXAMPLE 19

N$^\alpha$—Mes—D—Arg—Gly—Arg—pNA.2HCl

Molecular weight=658.60

(19a) N$^\alpha$—Mes—D—Arg(NO$_2$)—Gly—Arg(NO$_2$)—pNA

Molecular weight=675.66

0.5 mmol H—D—Arg(NO$_2$)—Gly—Arg(NO$_2$)—p-NA.Hcl (prepared according to example 17d) dissolved in 20 ml DMF and 0.6 mmol methanesulfonylchloride are treated in the same way and under the same reaction conditions as in example 17e.

Yield: 70%
TLC: Rf=0.47 (A).

19. N$^\alpha$—Mes—D—Arg—Gly—Arg—pNA.2HCl
Molecular weight=658.60

0.35 mmol N$^\alpha$—Mes—D—Arg(NO$_2$)—Gly—Arg(NO$_2$)—pNA (prepared according to example 19a) is deprotected and purified in the same way as in example 17.

Yield: 43.5%
TLC: Rf=0.48 (M)
HPLC: 97% purity
[α]=−17.6° (c=0.5%).

EXAMPLE 20

N$^\alpha$—Z—D—Arg—Sar—Arg—pNA.2HCl

Molecular weight=728.66

(20a) H—Sar—Arg—pNA.2HCl
Molecular weight=438.33

5 mmol Boc—SarOH, 5 mmol HOBT and 6 mmol DCCI are added to 5 mmol H—Arg—pNA.2HCl dissolved in 25 ml DMF and neutralized in cold (−10° C.) with Et$_3$N. The mixture is stirred for 1 hour in cold and at room temperature overnight. The DCU formed is filtered off and the solution is evaporated in vacuo to an oil, which is dissolved in 100 ml n-butanol, washed with 2% NaHCO$_3$, H$_2$O, 2% KHSO$_4$ and H$_2$O. After drying with Na$_2$SO$_4$, the n-butanol phase is evaporated and precipitated with diethylether. The precipitate is filtrated, washed with diethylether and dried. The substance is suspended in 25 ml HCl-solution (1.5M in AcOH) and stirred for 2 hours at room temperature, precipitated with diethylether and ion exchanged in the same way as in example 1.

Yield: 63.5%
TLC: Rf=0.15 (A).

20. N$^\alpha$—Z—D—Arg—Sar—Arg—pNA.2HCl
Molecular weight=728.66

3 mmol Z—D—ArgOH.HCl, 3 mmol HOBT and 3.5 mmol DCCI are added to 3 mmol Sar—Arg—p-NA.2HCl (prepared according to example 20a) dissolved in 30 ml DMF and neutralized in cold (−10° C.) with Et$_3$N. The mixture is stirred for 1 hour in cold and for 72 hours at room temperature. The DCU formed is filtered off and the solution is evaporated in vacuo. The product is ion exchanged and purified in the same way as in example 1.

Yield: 43%

TLC: Rf=0.2 (A).
HPLC: 99% purity
[α]=−24.7° (c=0.55%).

EXAMPLE 21

N$^α$—Z—D—Arg—Gly—CHA.2HCl

Molecular weight=729.65

(21a) Boc—Arg—CHA.HCl 3.2 mmol isobutyl chloroformate is added to 3.0 mmol Boc—Arg—CHA.HCl dissolved in 10 ml DMF and neutralized in cold (−10° C.). The reaction mixture is stirred for 15 minutes in cold and a mixture of 3 mmol 3-carboxy-4-hydroxianiline, 3 mmol NEM and 10 ml DMF are added. The reaction goes on under stirring for 2 hours in cold and at room temperature overnight. The solution is evaporated in vacuo to an oil. 50 ml n-butanol is added and the mixture is stirred for 3 hours at room temperature. The Boc—Arg—CHA.HCl formed is filtered off.

Yield: 50%
TLC: Rf=0.5 (A).

(21b) H—Arg—CHA.HCl
Molecular weight=382.25

8 ml 2N HCl in AcOH is added to 2 mmol Boc—Gly—Arg—CHA.HCl. The reaction goes on for 45 minutes at room temperature. The reaction mixture is evaporated in vacuo to an oil, which is dissolved in isopropanol and precipitated with EtOAc.

Yield: 97%
TLC: Rf=0.15 (A).

(21c) Boc—Gly—Arg—CHA.HCl
Molecular weight=502.95

2 mmol H—Arg—CHA.2HCl dissolved in 12 ml DMF is neutralized in cold (−10° C.) with NEM, whereafter 2.1 mmol Boc—Gly—ONp is added. The reaction goes on under stirring for 1 hour in cold and at room temperature overnight. The solution is evaporated in vacuo to an oil which is dissolved in 10 ml MeOH and precipitated with EtOAc.

Yield: 88%
TLC: Rf=0.4 (A).

(21d) H—Gly—Arg—CHA.2HCl
Molecular weight=439.30

10 ml 2N HCl in AcOH is added to 2 mmol Boc—Gly—Arg—CHA HCl. The reaction mixture is stirred for 45 minutes at room temperature and then precipitated in EtOAc.

Yield 98%
TLC: Rf=0.15 (A).

(21) N$^α$—Z—D—Arg—Gly—ARg—CHA.2HCl
Molecular weight=729.65

1 mmol H—Gly—Arg—CHA.2HCl dissolved in 10 ml DMF is neutralized in cold (−10° C.) with NEM, whereafter 1.1 mmol Z—D—Arg—ONp.HNO₃ is added. The reaction goes on for 1 hour in cold and for 2 hours at room temperature. The solution is evaporated in vacuo to an oil, which is precipitated with EtOAc. The product is purified on a Sephadex ® column with 10% AcOH as eluent and ion exchanged on a Sephadex ®QAE-25 column in chloride form with 50% EtOH as eluent.

Yield: 57%
TLC: Rf=0.21 (A)
HPLC: 99% purity
[α]=−18.6° (C=0.3%).

EXPERIMENTS

Determination of enzyme kinetic properties

The kinetic data for the substrates are determined by measuring the initial velocity of hydrolysis (Vi) at different substrate concentrations (Si) and at constant enzyme concentrations (Eo). The binding constant ($K_m$) and the maximum velocity ($V_{max}$) are obtained in known manner from Lineweaver-Burk-plot, then the $K_{cat}$ is calculated (Hemker H. C. loc. cit.)

Methods

Enzymes and substrates are mixed in a buffer solution at −37° C. The absorbance change per minute is measured at 405 nm in a spectrophotometer (pNA-substrate) or in a spectrofluorometer at excitation wavelength 380 nm and emission wavelength 440 nm (AMC-substrate).

The following commercially available reference substrates are used in the tests:

Reference substrates

S-2222: Bz—Ile—Glu—(γ—OR)—Gly—ARg—p-NA.HCl
R: H=50%; CH₃=50%.
KabiVitrum AB, Stockholm, Sweden.
CBS 31.39: CH₃SO₂—D—Leu—Gly—Arg—p-NA.AcOH
Diagnostica Stago, Asnieres s/Seine, France.

TEST 1

Determination of the Kinetic Constants for FX$_a$ bovine

FX$_a$ bovine (KabiVitrum) with a constant enzyme concentration
E₀=4 nmol/l (pNA-substrate)
E₀=2 nmol/l (AMC-substrate)
and the substrate in concentrations between 0.01-0.4 mmol/l (Si) are mixed in a trisbuffer solution 0.05 mol/l, pH=8.3, I=0.25 (NaCl) at 37° C. Absorbance change per minute is measured at 405 nm in a spectrophotometer for pNA-substrate and in a spectrofluorometer at emission wavelength 440 nm for AMC-substrate, respectively. From these values then $K_m$ and $K_{cat}$ are calculated, which are shown in table I.

Table I shows that the tripeptide substrates according to the invention possess a high affinity to the enzyme FX$_a$ bovine simultaneously as most of the substrates have a high rate of velocity. The selectivity constant $K_{cat}/K_m$ states that the new substrates show a better selectivity for FX$_a$ bovine than S-2222 and that even most of the new substrates are superior to CBS 31.39.

TEST 2

Determination of Kinetic Constants for FX$_a$ Human

The substrates in concentrations between 0.1-0.7 mmol/l (Si) are mixed with FX$_a$ human plasma and treated according to the method as described by Aurell; L., et al. (Perspectives in Hemostatis, Ed. Fareed J. et al, New York, Pergamon Press 1981, p. 382-388).

10 μl test plasma, control or standard and 200 μl trisbuffer solution (0.05 mol/l tris, pH 7.0, I=0.25 (NaCl)), polybrene (0.1 g/l) are mixed and incubated at 37° C. for 2-4 minutes. 200 μl substrate (37° C.) in concentrations between 0.1-0.7 mmol/l dissolved in trisbuffer solution prepared according to the above are added. The mixture is well stirred and within 30 seconds 200 μl RVV+CaCl₂ (20°-25° C.) are added and the mixture is stirred. The absorbance change is measured at once in a spectrophotometer at 405 nm and 37° C.

The results are shown in table II.

Table II shows that the new tripeptide substrates possess a superior affinity for enzyme $FX_a$ human compared with the reference substrates simultaneously as they also show a high rate of velocity, which makes them superior to the commercially available substrates.

TEST 3

Determination of Thrombin Sensitivity

At the determination of FX in plasma there is always a risk for formation of active thrombin in which disturbes the $FX_a$ determination.

Thrombin bovine (KabiVitrum) with a constant concentration $E_0=1.3$ nmol/l and the substrates in concentrations between 0.1-0.4 mmol/l (Si) are mixed in a trisbuffer solution (0.05 mol/l, pH=8.3, I=0.25 (NaCl) at 37° C. The test is performed according to test 1.

The absorbance change per minute is measured at 405 nm in a spectrophotometer and the $K_m$ and $K_{cat}$-values are calculated as shown in table III.

Table III shows that the ratio for the selectivity constant $FX_a$ bovine through thrombin for the new tripeptide substrates can be compared with the tetrapeptide and are superior to the known tripeptide when the sensitivity for $FX_a$ bovine is compared to thrombin.

TEST 4

Solubility

The solubility in water and trisbuffer solution (0.05 mol/l, pH=8.3, I=0.25 (NaCl)), respectively at 25° C. for some new substrates are shown in tabel IV compared with the tetrapeptide substrate S-2222.

The table shows that the new tripeptide substrates have a clearly higher solubility in water as well as in buffer solution compared with the tetrapeptide S-2222.

TABLE I

| Substrate Ex. no. | $K_m$ mmol/l | $K_{cat}$ sek⁻¹ | $K_{cat}/K_m$ 1/μmol·sek |
|---|---|---|---|
| S-2222 | 0.51 | 180 | 0.35 |
| 1 | 0.11 | 250 | 2.27 |
| 2 | 0.22 | 180 | 0.82 |
| 4 | 0.19 | 270 | 1.42 |
| 5 | 0.26 | 280 | 1.07 |
| 6 | 0.21 | 350 | 1.66 |
| 7 | 0.45 | 245 | 0.55 |
| 8 | 0.22 | 230 | 1.04 |
| 9 | 0.15 | 310 | 2.06 |
| 10 | 0.20 | 210 | 1.05 |
| 11 | 0.27 | 260 | 0.96 |
| 12 | 0.12 | 140 | 1.14 |
| 13 | 0.19 | 170 | 0.89 |
| 16 | 0.04 | 110 | 2.75 |
| 18 | 0.16 | 225 | 1.41 |
| 19 | 0.17 | 200 | 1.17 |
| 20 | 0.16 | 220 | 1.37 |
| CBS 31.39 | 0.29 | 290 | 1.00 |

TABLE II

| Substrate Ex. no. | $K_m$ μmol/l | $V_{max}$ μmol/l min | $V_{max}/K_m$ min⁻¹ |
|---|---|---|---|
| S-2222 | 1970 | 46 | 0.023 |
| 1 | 380 | 73 | 0.192 |
| 4 | 340 | 46 | 0.135 |
| 9 | 210 | 51 | 0.242 |
| 16 | 50 | 15 | 0.300 |
| CBS 31.39 | 1060 | 61 | 0.057 |

TABLE III

| Substrate Ex. No. | $K_m$ mmol/l | $K_{cat}$ sek⁻¹ | $K_{cat}/K_m$ 1/μmol·sek | $\frac{K_{cat}/K_m FX_a \text{ bovine}}{K_{cat}/K_m \text{ thrombin}}$ |
|---|---|---|---|---|
| S-2222 | 0.71 | 13 | 0.018 | 19.4 |
| 1 | 0.13 | 13 | 0.100 | 22.7 |
| 4 | 0.41 | 23 | 0.056 | 25.4 |
| 9 | 0.073 | 11 | 0.151 | 13.6 |
| 16 | 0.16 | 17 | 0.106 | 25.9 |
| CBS 31.39 | 0.23 | 72 | 0.313 | 3.2 |

TABLE IV

| Substrate Ex. no. | Relative solubility | |
|---|---|---|
| | water | tris-buffer |
| S-2222 | 1 | 1 |
| 1 | >7 | >5 |
| 4 | >7 | >10 |
| 9 | >3 | >3 |
| 16 | >5 | >10 |

We claim:

1. Tripeptide derivative characterized by the general formula:

$$R_1-X-D-Arg-A-Arg-NH-R_2$$

wherein $R_1$ is hydrogen, α- or β-naphtyl residue, lower alkyl residue which may be substituted with a carboxyl group, unsubstituted or substituted phenyl- or phenylalkyl residue, wherein the alkyl group having 1 to 4 carbon atoms and wherein said substituted phenyl is a phenyl substituted with a lower alkyl, lower alkoxy, halogen or nitro group

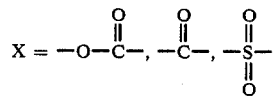

or a single bond with the proviso that when
$R_1$ is hydrogen then X is a single bond
A=Gly or Sar
$R_2$=an aromatic or heterocyclic residue which in conjunction with the NH moiety to which it is connected gives a compound $R_2-NH_2$ by enzymatic hydrolysis, which can be determined quantitatively,
or disalts and trisalts of inorganic or organic acids thereof.

2. Tripeptide derivative according to claim 1 characterized in that A is Gly.

3. Tripeptide derivative according to claim 1 characterized in that X is an oxycarbonyl- or sulfonyl group.

4. Tripeptide derivative according to claim 1 characterized in that $NH_2-R_2$ is a chromogenic or a fluorogenic group.

5. Tripeptide derivative according to claim 4 characterized in that $NH_2-R_2$ is pNA, AMC or CHA.

6. Tripeptide derivative according to claim 1 characterized in that $R_1$ is ethyl, benzyl or tert. butyl.

7. Tripeptide derivative according to claim 1 in the form of disalts.

8. Tripeptide derivative according to claim 1 which is $N^\alpha$—Bzls—D—Arg—Gly—Arg—pNA.2HCl.

9. Tripeptide derivative according to claim 1 which is $N^\alpha$—Mos—D—Arg—Gly—Arg—pNA.2HCl.

10. Tripeptide derivative according to claim 1 which is $N^\alpha$—Ets—D—Arg—Gly—Arg—pNA.2HCl.

11. Tripeptide derivative according to claim 1 which is $N^\alpha$—Z—D—Arg—Gly—Arg—pNA.2HCl.

12. Tripeptide derivative according to claim 1 which is $N^\alpha$—Boc—D—Arg—Gly—Arg—pNA.2HCl.

13. Tripeptide derivative according to claim 2 characterized in that X is an oxycarbonyl- or sulfonyl group.

14. Tripeptide derivative according to claim 2 characterized in that $NH_2$—$R_2$ is a chromogenic or a fluorogenic group.

15. Tripeptide derivative according to claim 3 characterized in that $NH_2$—$R_2$ is a chromogenic or a fluorogenic group.

16. Tripeptide derivative according to claim 2 characterized in that $NH_2$—$R_2$ is pNA, AMC, or CHA.

17. Tripeptide derivative according to claim 3 characterized in that $NH_2$—$R_2$ is pNA, AMC, or CHA.

18. Tripeptide derivative according to claim 2 characterized in that $R_1$ is ethyl, benzyl or tert. butyl.

19. Tripeptide derivative according to claim 3 characterized in that $R_1$ is ethyl benzyl or tert. butyl.

20. Tripeptide derivative according to claim 4 characterized in that $R_1$ is ethyl, benzyl or tert. butyl.

21. Tripeptide derivative according to claim 5 characterized in that $R_1$ is ethyl, benzyl or tert. butyl.

22. The tripeptide derivative of claim 1 wherein said substituted phenyl is substituted in the para position in the phenyl ring.

* * * * *

UNITED STATES PATENT AND TRADEMARK OFFICE
CERTIFICATE OF CORRECTION

PATENT NO.    : 4,797,472
DATED         : January 10, 1989
INVENTOR(S)   : Gustavsson, et al.

It is certified that error appears in the above-identified patent and that said Letters Patent is hereby corrected as shown below:

Column 2, line 48 delete the term "Factor $Z_a$" and insert therefore the term "Factor $X_a$".

Column 4, lines 8 and 53 delete the term "Box" and insert therefore the term "Boc".
Column 4, line 32 delete the term "Ps" and insert therefore the term "Ns".

Column 5, line 31 change "ARg" to "Arg".
Column 5, line 31 change "Hbr" to "HBr".

Column 6, line 1 change "9%" to "97%".

Column 7, line 43 delete the hyphen between AMC and .2 HCl.

Column 8, line 47 change "(17a)" to "(17b)".
Column 8, line 61 change "(17a)" to "(17c)".
Column 8, line 67 "Box" should read "BOC".

Column 9, line 12 delete the hyphen between Arg and ($NO_2$).
Column 9, line 12 "Box" should read "BOX".

Column 9, line 34 add a dot between pNA and 2 HCl.
Column 9, line 37 add "to" between according and example 17c.
Column 9, line 56 add a full stop between 669.63 and 0.6 mmol.
Column 9, line 60 change "(31 10°C)" to "-10°C".

Column 11, line 47 add a dot between CHA and HCl.
Column 11, line 52 change "ARg" to "Arg".

Column 12, line 15 change "-37°C" to "+37°C".
Column 12, line 24 change "ARg" to "Arg".

Column 13, line 36 change "tabel" to "table".

UNITED STATES PATENT AND TRADEMARK OFFICE
CERTIFICATE OF CORRECTION

PATENT NO. : 4,797,472

DATED : January 10, 1989

INVENTOR(S) : Gustavsson, et al

It is certified that error appears in the above-identified patent and that said Letters Patent is hereby corrected as shown below:

Column 15, line 7 change "Mos" to "Moz".

Signed and Sealed this

Twenty-fourth Day of December, 1991

*Attest:*

HARRY F. MANBECK, JR.

*Attesting Officer*  *Commissioner of Patents and Trademarks*